United States Patent [19]

Pachaly et al.

[11] Patent Number: 5,288,892
[45] Date of Patent: Feb. 22, 1994

[54] SEPARATION OF METHYLCHLOROSILANES FROM HIGH BOILING RESIDUES OF METHYLCHLOROSILANE SYNTHESIS

[75] Inventors: Bernd Pachaly; Anton Schinabeck, both of Burghausen, Fed. Rep. of Germany

[73] Assignee: Wacker-Chemie GmbH, Munich, Fed. Rep. of Germany

[21] Appl. No.: 48,597

[22] Filed: Apr. 19, 1993

[30] Foreign Application Priority Data

Jun. 19, 1992 [DE]  Fed. Rep. of Germany ....... 4220151

[51] Int. Cl.$^5$ ............................................. C07F 7/08
[52] U.S. Cl. ................................. 556/466; 556/468
[58] Field of Search ........................... 556/466, 468

[56] References Cited

U.S. PATENT DOCUMENTS

| | | | |
|---|---|---|---|
| 2,709,176 | 5/1955 | Bluestein | 556/468 |
| 3,432,537 | 3/1969 | Guinet et al. | 556/468 |
| 3,772,347 | 11/1973 | Atwell et al. | 260/448.2 E |
| 3,878,234 | 4/1975 | Atwell et al. | 556/468 |
| 4,297,500 | 10/1981 | Finke et al. | 556/466 |
| 4,552,973 | 11/1985 | Feldner et al. | 556/469 |

FOREIGN PATENT DOCUMENTS 1093399 5/1955 France .

OTHER PUBLICATIONS

Chemie und Technologie der Silicone, W. Noll, 1968, pp. 35–36.
Chemistry and Technology of Silicones, W. Noll, 1968, pp. 38–40.
Calas et al., "Some Practical Uses of the Disilane Residue from the Direct Synthesis of Methylchlorosilanes", 1982, pp. 117–130.

*Primary Examiner*—Paul F. Shaver

[57] ABSTRACT

A process for separating methylchlorosilanes from high boiling residues from the methylchlorosilane synthesis, in which cleavable methylchlorodisilanes which are present in the residues and which have at least two chlorine atoms attached to one silicon atom are cleaved with hydrogen chloride in the presence of a catalyst which remains in the reaction mixture, which comprises cleaving the methylchlorodisilanes in the presence of by-products which are more volatile than the cleavable methylchlorodisilanes in the high boiling residues from the methylchlorosilane synthesis which have a boiling point of at least 70° C. under normal conditions and continuously removing the more volatile by-products from the reaction mixture along with the methylchlorosilanes and the noncleavable methylchlorodisilanes.

2 Claims, 2 Drawing Sheets

SEPARATION OF METHYLCHLOROSILANES FROM HIGH BOILING RESIDUES OF METHYLCHLOROSILANE SYNTHESIS

The invention relates to an improved process for separating methylchlorosilanes from the high boiling residues of the methylchlorosilane synthesis and more particularly to a process for separating methylchlorosilanes from high boiling methylchlorosilanes which are formed as by-products in the direct synthesis of methylchlorosilanes.

BACKGROUND OF THE INVENTION

The direct synthesis of methylchlorosilanes from silicon and methyl chloride at 250° to 300° C. using copper catalysts produces not only methylchlorosilanes of the general formula $Me_xSiCl_{4-x}$, where x is from 0 to 4, but also various hydrogensilanes and high boiling by-products, primarily methylchlorodisilanes of the general formula $Me_xSi_2Cl_{6-x}$, where x is from 2 to 5.

The methylchlorosilanes are separated and purified by distillation. The distillation leaves a high boiling fraction which accounts for from 5 to 10% of crude product. It is economically and ecologically desirable to further treat these residues to isolate useful materials. This is achieved by separating the distillable methylchlorodisilanes and cleaving them with hydrogen chloride into methylchlorosilanes. In general, this cleavage is carried out with amine catalysts in the liquid phase. The work-up of the residue is described inter alia in W. Noll, (Chemistry and Technology of Silicones) 2nd Edition 1968, Academic Press, Inc., Orlando, Chap. 2.2.8. The chemical properties of disilanes and the fundamental principles of cleavage are described in R. Calas et al., J. Organomet. Chem. 225 (1982) 117–130.

Usually the high boiling fraction is worked up using a batchwise distillation in order to isolate the methylchlorodisilane fraction which is cleavable with hydrogen chloride. This distillation gives rise to the following fractions:

| Boiling range | Main components |
| --- | --- |
| 70–140° C. Fraction 1 | Dimethyldichlorosilane Ethylmethyldichlorosilane Methylpropyldichlorosilane Ethyldimethylchlorosilane Methylchlorodisilanes Hydrocarbons |
| 140–155° C. Fraction 2 | Pentamethylchlorodisilane Tetramethyldichlorodisilane Trimethyltrichlorodisilane Dimethyltetrachlorodisilane |
| 155–160° C. Fraction 3 | Trimethyltrichlorodisilane Dimethyltetrachlorodisilane |
| >160° C. Fraction 4 | Oligomethylsilanes, including dimethyltetrachlorodisilane Carbosilanes Siloxanes Metals and metal halides |

Only those methylchlorodisilanes which have at least two chlorine atoms attached to one silicon atom, i.e., not the symmetrical tetramethyldichlorodisilane or pentamethylchlorodisilane are cleavable with hydrogen chloride to form monosilanes having the equation

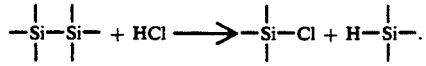

The cleavage product comprises essentially dimethyldichlorosilane, methyltrichlorosilane and methylchlorodisilane.

The cleavage of the cleavable disilanes of fraction 3 is conducted in reaction vessels in which it is possible to remove the cleavage product mixture, for example in a distillation flask with an attached column. The distillation removes the cleavage product silane at the top of the column, while noncleavable components of the disilane feed mixture build up in the reaction mixture and necessitate regular evacuation of the contents from the reactor.

Those fractions from the work-up of the high boiling residues which contain little if any cleavable disilanes, in particular fraction 4, as well as the disilane cleavage residue to be evacuated which still contains cleavable disilanes have to be disposed of by incineration.

Therefore, it is an object of the present invention to provide a process for separating methylchlcrosilanes from high boiling residues from the methylchlorosilane synthesis. Another object of the present invention is to provide a process for separating methylchlorosilanes from high boiling residues from the methylchlorosilanes synthesis in which the cleavable methylchlorodisilanes can be cleaved continuously to form a higher yield of silanes from the cleavage product.

SUMMARY OF THE INVENTION

The foregoing objects and others which will become apparent from the following description are accomplished in accordance with this invention, generally speaking, by providing a process for separating methylchlorosilanes from high boiling residues containing methylchlorodisilanes which are obtained from the methylchlorosilane synthesis, in which cleavable methylchlorodisilanes which are present in the residues and which have at least two chlorine atoms attached to one silicon atom are cleaved with hydrogen chloride in the presence of a catalyst which is present in the reaction mixture, the improvement which comprises cleaving the methylchlorodisilanes in the presence of by-products which are more volatile than the cleavable methylchlorodisilanes in the high boiling residues from the methylchlorosilane synthesis which have a boiling point of at least 70° C. under normal conditions while continuously removing the more volatile by-products from the reaction mixture together with the methylchlorosilanes and the noncleavable methylchlorodisilanes.

DESCRIPTION OF THE INVENTION

The more important by-products in the high boiling methylchlorosilane synthesis residue which are more volatile than the cleavable methylchlorodisilanes and have a boiling point of at least 70° C. under normal conditions are listed in fractions 1 and 2 above. Additional by-products of this type, which are likewise distillable within the boiling range of from 70° to 155° C., are in minimal amounts.

The presence of the methylchlorosilanes in the high boiling residues, of the by-products which are more volatile than the cleavable methylchlorodisilanes, and of the noncleavable methylchlorodisilanes does not interfere with the cleavage process. For this reason the separation of the high boiling residues to isolate a fraction which contains essentially only cleavable methylchlorodisilanes (fraction 3) generally employed heretofore is not necessary. Continuous removal from the reaction mixture of all compounds which are lower boiling than the cleavable methylchlorodisilanes makes it possible for the cleavage process to be operated continuously, since all the compounds which are higher boiling than the cleavable methylchlorosilanes and the catalyst (fraction 4) are removed prior to the cleavage process.

Catalysts which are suitable for cleaving methylchlorodisilanes with hydrogen chloride and remain in the reaction mixture can be selected from slightly volatile homogeneous or heterogeneous catalysts known per se. Examples are transition metal complexes such as $(Me_2PhP)_2PdCl_2$, $(Ph_3P)_2NiCl_2$ and $(Ph_3P)_4Pd(O)$ and the preferred organic nitrogen compounds such as N-methyl-2-pyrrolidone, polyvinylpyrrolidone, alkylated amides and tertiary amines.

Particularly preferred catalysts are tertiary amines which have at least one optionally fluorine-, chlorine- or $C_{1-6}$alkyl-substituted aryl radical of preferably up to 18 carbon atoms, such as phenyl, naphthyl or p-tolyl, and in which any alkyl radicals present on the nitrogen atom preferably have up to 18 carbon atoms and may be fluorine- or chlorine-substituted. Preferred examples are tributylamine and N,N-dimethylaniline.

The advantages of the process of this invention are shown hereinafter by comparing a known method for working up high boiling residues of methylchlorosilane synthesis with a preferred embodiment of the process of the invention.

BRIEF DESCRIPTION OF THE DRAWINGS

FIG. 1 shows a known process:

Line (1) transfers the crude silane mixture from the reaction of silicon with methyl chloride into column (2). Column (2) gives rise to the high boiling residues (high boiler). This high boiler passes via line (3) into column (4).

Due to the required absence of high boilers from the head product of column (2), the high boiler contains a relatively high proportion of the useful product of the direct synthesis, dimethyldichlorosilane. The high boiler is then separated by batchwise distillation in column (4). This produces in lines 5, 6 and 7 the aforementioned fractions 1, 2 and 4 respectively as waste streams, in which not only dimethyldichlorosilane is lost but also a significant proportion of the cleavable disilanes. Fraction 3 passes via line (8) into the disilane cleavage reactor (9) where it is cleaved with hydrogen chloride using an amine catalyst.

Noncleavable constituents of fraction 3 have to be regularly evacuated from the reactor (9) via line 10, and likewise constitute a waste product. The cleavage product silane is separated off via the column of reactor (9) and via line (11) and reunited with the crude silane from the direct synthesis.

Figure 1:
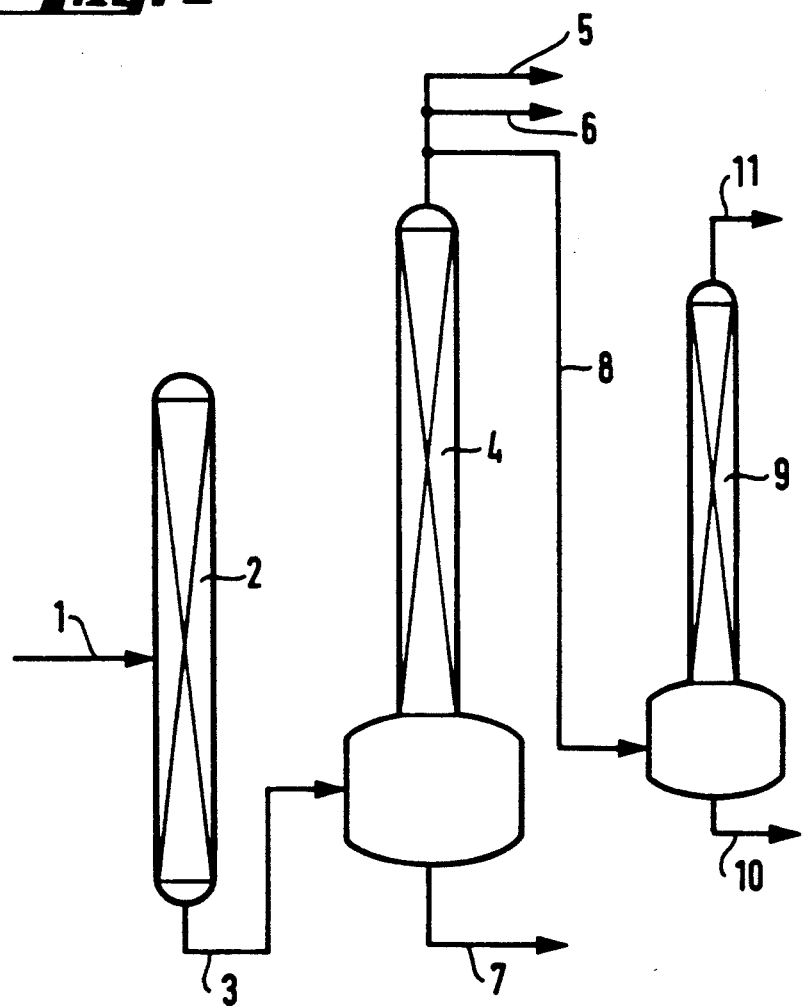
FIG. 1—illustrates a conventional process for separating methylchlorosilanes
Figure 2:
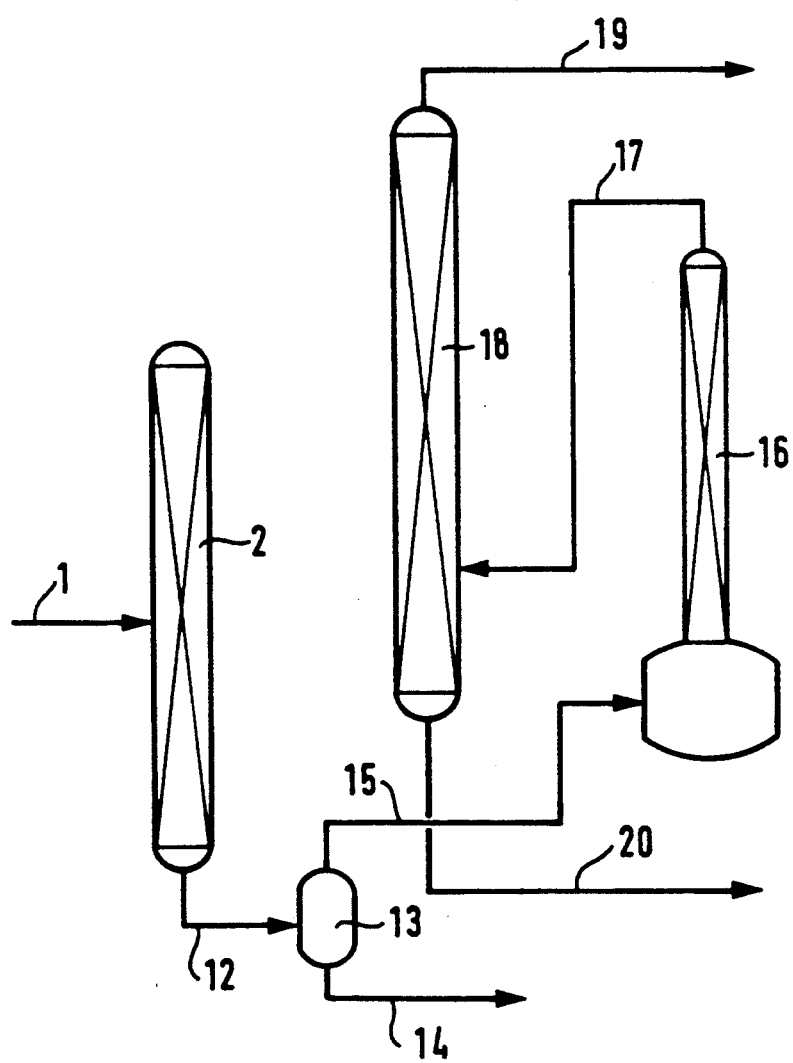
FIG. 2—illustrates a process for separating methylchlorosilanes in accordance with this invention.

FIG. 2 shows the process of the present invention:

Line (1) transfers the crude silane mixture into column (2). There the high boiling portion is separated off and fed via line (12) into a continuous vaporizer (13), in which fraction 4 is separated off via line (14), and the volatile portion fed via line (15) into the disilane cleavage reactor (16). Here all the cleavable disilanes are cleaved, while the noncleavable disilanes and other constituents of fractions 1 and 2 are separated off at the top of the column together with the cleavage product silane and fed via line (17) into the distillation column (18). In column (18) the cleavage product silane is separated off overhead and fed via line (19) into the crude silane mixture. The bottom product evacuated via line (20) comprises fractions 1 and 2.

Advantages of the process of this invention are:

(1) There is no need for an energy- and capital- intensive sharp distillation separation, (2) reduction in the thermal stress of a long residence time, such as in the batch-wise high boiler distillation, suppresses secondary reactions, (3) a portion of the useful product dimethyldichlorosilane inevitably entrained in the high boiler remains in the cleavage product silane and is not lost, (4) the cleavable disilanes present in fractions 1, 2 and 4 are all cleaved and not lost, (5) column (18) and cleavage reactor (16) can be operated continuously, resulting in an increase in capacity, and (6) the proportion of waste which cannot be utilized is significantly reduced.

The practice of cleaving the methylchlorodisilanes in the cleavage reaction (9) is illustrated hereinafter:

EXAMPLE 1

PROCESS WHICH IS NOT IN ACCORDANCE WITH THE INVENTION

A 5000 l capacity cleavage reactor is charged with 700 kg/hr of a mixture containing 7% of tetramethyldichlorodisilane, 46.5% of trimethyltrichlorodisilane and 46.5% of dimethyltetrachlorodisilane, in which the base column temperature is 120° C. and the top column temperature is 80° C. and the top column pressure is 0.15 MPa (abs.), under a reflux of 1000 l/hr. At the start of the run 50 kg of tributylamine were added to the reactor. HCl gas is metered in in such a way as to produce a small amount of waste gas, about 110 kg/hr. The distillate obtained comprises 760 kg/hr of cleavage product silane comprising 45% of methyldichlorosilane, 28% of methyltrichlorosilane and 27% of dimethyldichlorosilane. After 100 hrs the reactor is filled to capacity with noncleavables and the run has to be discontinued.

EXAMPLE 2

PROCESS IN ACCORDANCE WITH THE INVENTION

The cleavage reactor of Example 1 is charged with 1000 kg/hr of a mixture containing 11% of dimethyldichlorosilane, 5.6% of medium boilers (boiling range 75°–145° C.), 5.6% of tetramethyldichlorosilane, 38.9% of trimethyltrichlorodisilane and 38.9% of dimethyltetrachlorodisilane, in which the base column temperature is 140° C. and the top column temperature is 90° C. and the top column pressure is 0.15 MPa (abs.), under a reflux rate of 700 l/hr. The reactor had beforehand been charged with 50 kg of tributylamine. HCl gas is metered in in such a manner as to produce a small amount of waste gas, about 130 kg/hr. The distillate obtained comprises 1130 kg/hr of cleavage product silane comprising 38% of methyldichlorosilane, 30% of dimethyldichlorosilane, 23% of methyltrichlorosilane, 4.5% of medium boilers and 4.5% of tetramethyldichlorodisilane. The fill level in the reactor remains constant and the run can be continued without interruption.

What is claimed is:

1. An improved process for separating methylchlorosilanes from high boiling residues form the methylchlorosilane synthesis, in which cleavable methylchlorodisilanes which are present int he residues and which have at least two chlorine atoms attached to one silicon atom are cleaved with hydrogen chloride in the presence of a catalyst which remains in the reaction mixture, the improvement which comprises separating the methylchlorosilane synthesis by-products having a boiling point of at least 70°$\pi$C. under normal conditions and containing methylchlorodisilanes from the high boiling residues having a boiling point above 160° C., cleaving the methylchlorodisilanes in the presence of the by-products which are more volatile than the cleavable methylchlorodisilanes and continuously removing the more volatile by-products from the reaction mixture along with the methylchlorosilanes and the noncleavable methylchlorodisilanes.

2. The process of claim 1, wherein the catalyst is a tertiary amine.

* * * * *